(12) United States Patent
Pasquet-Vallejo

(10) Patent No.: US 7,754,486 B2
(45) Date of Patent: Jul. 13, 2010

(54) CULTURE MEDIUM NAMED MV06 FOR BOTH ENDOTHELIAL AND MYOCARDIAC CELLS

(75) Inventor: Stéphanie Pasquet-Vallejo, Mulhouse (FR)

(73) Assignee: Institut de Recherche en Hematologie et Transplantation, Mulhouse (FR)

( * ) Notice: Subject to any disclaimer, the term of this patent is extended or adjusted under 35 U.S.C. 154(b) by 456 days.

(21) Appl. No.: 11/645,482

(22) Filed: Dec. 26, 2006

(65) Prior Publication Data

US 2008/0153164 A1    Jun. 26, 2008

(51) Int. Cl.
C12N 5/00    (2006.01)
C12N 5/02    (2006.01)
(52) U.S. Cl. .................. 435/405; 435/404; 435/408
(58) Field of Classification Search .................. None
See application file for complete search history.

(56) References Cited

U.S. PATENT DOCUMENTS 6,110,459 A * 8/2000 Mickle et al. ............ 424/93.21
2006/0166361 A1 * 7/2006 Seyda et al. ................ 435/366

OTHER PUBLICATIONS

Hernandez et al. Human Endothelial Cell Cultures from Progenitor Cells Obtained by Leukapheresis, 42$^{nd}$ Annual Meeting, Midwest Surgical Association, Aug. 15-18, 1999, pp. 355-359.
Peichev et al. "Expression of VEGFR-2 and AC133 by Circulating Human CD34+ Cells Identifies a Population of Functional Endothelial Precursors", Blood, vol. 95, Feb. 1, 2000, pp. 925-958.
Badroff et al. "Transdifferentiation of Blood-Derived Human Adult Endothelial Progenitor Cells into Functionally Active Cardiomyocytes", American Heart Association, Nov. 11, 2002, pp. 1024-1032.
Yoon et al. "Clonally Expanded Novel Multipotent Stem Cells from Human Bone Marrow Regenerate Myocardium after Myocardial Infraction", The Journal of Clinical Investigation, vol. 115 No. 2, Feb. 2005, pp. 329-338 and attachments.
Porat et al. "Isolation of an Adult Blood-Derived Progenitor Cell Population Capable of Differentiation into Angiogenic, Myocardial and Neural Lineages", British Journal of Haematology, 2006, pp. 1-12.

* cited by examiner

*Primary Examiner*—David M. Naff
*Assistant Examiner*—Debbie K Ware
(74) *Attorney, Agent, or Firm*—Davis & Bujold, P.L.L.C.

(57) ABSTRACT

A culture medium named MV06 enabling growth in vitro of both endothelial progenitor and myocardiac progenitor cells, composed of: Iscove's Modified Dubellco's Medium, Fetal calf serum, Horse serum, L-Glutamin (200 mM (100×)) Penicillin (10000 u/mL)/Streptomycin (1000 μg/mL), Hu-R Bone Morphogenetic Protein 2 (BMP-2), Hu-R Fibroblast Growth Factor 2 (FGF2), and Hu-R Vascular Endothelial Growth Factor (VEGF).

20 Claims, 2 Drawing Sheets

* p≤0,05 vs d0
*** p<0,01 vs d0

CULTURE MEDIUM NAMED MV06 FOR BOTH ENDOTHELIAL AND MYOCARDIAC CELLS

FIELD OF THE INVENTION

The present invention relates to a culture medium named MV06 enabling in vitro growth of both endothelial and myocardiac progenitor cells, from CD34+ cells.

BACKGROUND OF THE INVENTION

For the purpose of further clinical applications, it is requested to proceed to a differentiation and an ex-vivo expansion of endothelial and myocardiac progenitor cells from CD34+ cells previously purified by immunoselection.

A crucial issue is to prove that the dedicated differentiation and the functional capacities of CD34+ cell subsets would not be modified after ex-vivo expansion.

PRIOR ART

Various culture media have been reported in the literature as capable of inducing in vitro differentiation of human adult stem cells either into endothelial cells or cardiac muscle cells.

For endothelial Cells, Hernandez et al. have developed a culture medium allowing the differentiation of mononuclear cells (MNC), yielded from blood apheresis, into endothelial cells. Here, MNC were cultured on gelatine or fibronectin in M199 medium supplemented with Fetal Calf Serum (FCS), insulin, transferrin, endothelial all-growth supplement, and heparin.

Porat et al. also used human peripheral blood MNC for endothelial cell differentiation after culture on X-VIVO15® medium, supplemented with autologous serum, Vascular Endothelial Growth Factor (VEGF) and heparin. Cells were cultured in dishes previously coated with fibronectin or autologous plasma.

Endocult® is a medium commercialized by Stem Cells Technologies to generate CFU-Endothelial Cells (CFU-EC). This medium allows the quantification of endothelial stem cell sub-populations either circulating in peripheral blood (PB) or existing in bone marrow among total MNC. However, this culture method appears to be inappropriate when plating purified blood CD34+ cells instead of MNC, as they undergo apoptosis after 2 days only in these culture conditions.

From his side, Peichev et al. succeeded to induce a significant endothelial differentiation from human PB-CD34+ cells, using M199 medium supplemented with Fetal Bovine Serum (FBS), Fibroblast Growth Factor 2 (FGF2), and heparin in collagen-coated dishes.

For cardiac muscle cells, only a very few groups have developed culture media allowing in vitro differentiation of human adult stem cells into cardiac muscle cells:

A part endothelial differentiation, the group of Porat was also interested in differentiating PB-MNC into cardiac muscle cells and used a medium containing 5-azacytidine. But this method does not promote spontaneous stem cell differentiation as 5-azacytidine is a mutagen agent. Furthermore, this mutagenic mechanism would also render a further eventual clinical use of differentiated cells dangerous.

Another way used for in vitro differentiation of human adult stem cells into cardiomyocytes is co-culturing stem cells with newborn-rat cardiomyocytes in primary culture. Yoon et al. used this method to induce cardiac differentiation of human bone marrow cell lines, as did Badorff et al. but using human PB CD34+ cells yielded by apheresis. However, such co-culture of human cells and rat cells may promote a mechanism of fusion between the two cell types, which makes such a method for further potential clinical use inappropriate.

Thus, even when considering all these culture assays, nobody has developed today one sole medium having the capacity to induce both endothelial and cardiac muscle cell differentiation for so-called hematopoietic stem cells, in a way similar to what might occur after intra-myocardic cell reinjection.

EXPLANATION OF THE INVENTION

The MV06 culture medium enabling growth in vitro of both endothelial and myocardiac progenitor cell, according to the Invention is composed of:

Iscove's Modified Dubellco's Medium

Fetal calf serum

Horse serum

L-Glutamin 200 mM (100×)

Penicillin (10000 u/mL)/Streptomycin (1000 μg/mL)

Human-recombinant (hu-R) Bone Morphogenic Protein-2 (BMP-2)

Hu-R Fibroblast Growth Factor-2 (FGF2)

Hu-R Vascular Endothelial Growth Factor (VEGF)

According to a preferred manner to realize the culture of the Invention, the Iscove's modified Dubellco's medium represents 83% of the volume.

According to a preferred manner to realize the culture of the Invention, the fetal calf serum represents 12.5% of the volume.

According to a preferred manner to realize the culture of the Invention, the horse serum represents 2.5% of the volume.

According to a preferred manner to realize the culture of the Invention, the L-Glutamin 200 mM (100×) represents 1% of the volume.

According to a preferred manner to realize the culture of the Invention, the Penicillin (10000 u/mL)/Streptomycin (1000 μg/mL) represents 1% of the volume.

According to a preferred manner to realize the culture of the Invention, the Hu-R BMP-2 has a concentration of 1 ng/mL.

According to a preferred manner to realize the culture of the Invention, the Hu-R FGF2 has a concentration of 5 ng/mL According to a preferred manner to realize the culture of the Invention, the hu-R VEGF has a concentration of 10 ng/mL.

According to an advantageous manner to realize the Invention, the culture is made on an extra-cellular matrix composed of:

Fibronectin

Gelatine

Preferably, fibronectin represents 0.0005% of the volume and gelatine represents 0.02% of the volume.

Advantageously, gelatine is of type B, from bovine skin.

The composition of the present invention is appreciated for its capacity both to maintain CD34+ cells alive in culture for 7 days and more and to commit those cells into endothelial and cardiac muscle differentiation ways. FGF2 and VEGF are used for endothelial differentiation; BMP-2 (known to be a major inducer for cardiac differentiation during embryonic development) and FGF2 are used for cardiac muscle differentiation. Additionally, both fibronectin and gelatine coat culture dishes in an attempt to more or less closely reproduce the post-infarct cardiac tissue scare.

BRIEF DESCRIPTION OF THE DRAWINGS

The present invention and its advantages will be more apparent from the following description of a preferred embodiment, with reference to the attached drawings, provided by the way of non-limiting examples, wherein.

ILLUSTRATION OF THE INVENTION

The MV06 culture medium which was developed according to the present invention allows in vitro differentiation of both endothelial and myocardiac progenitor cells from CD34+ cells, as demonstrated by their significant expression of gene markers of each cell type.

Figure 1:
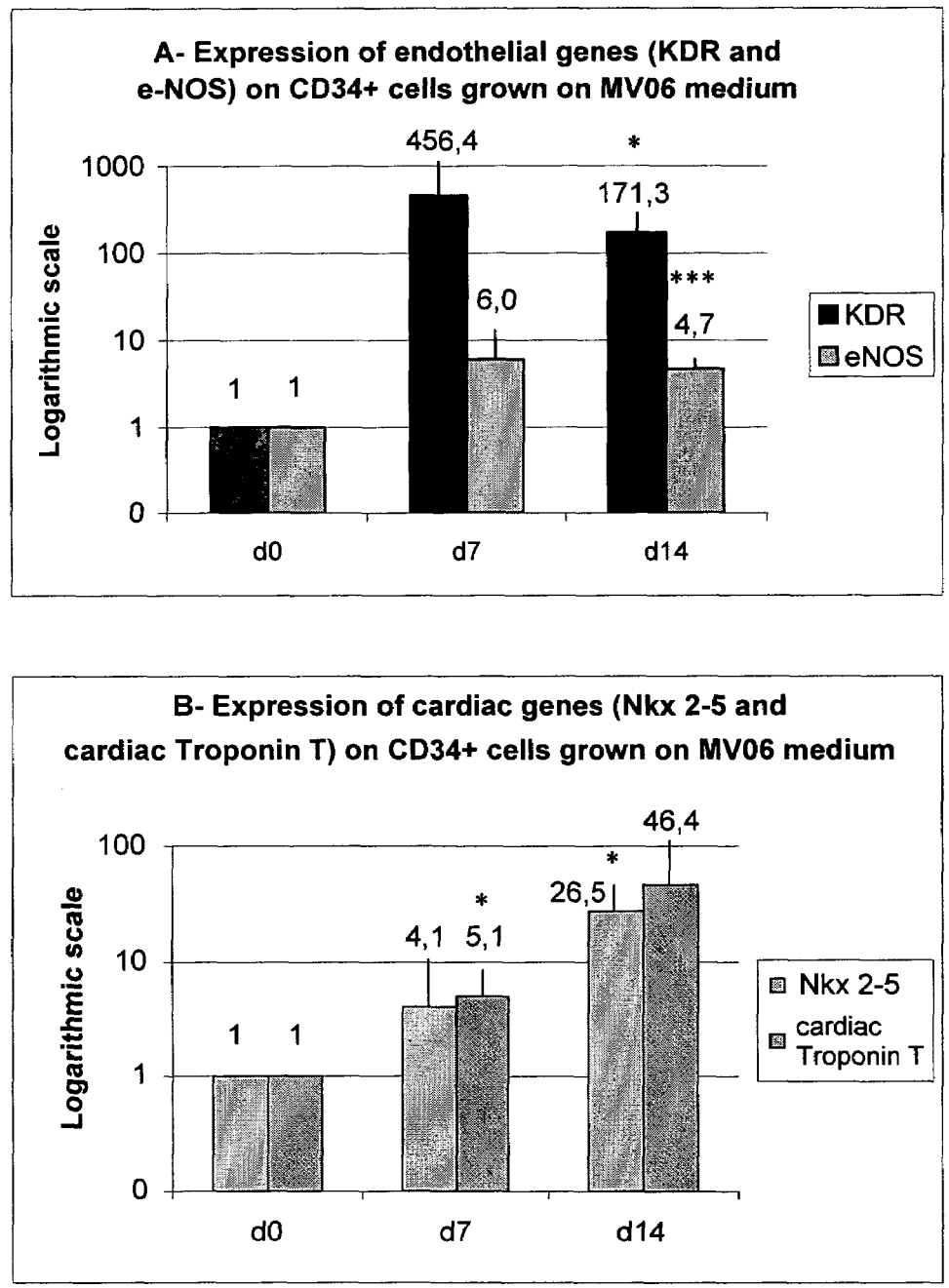
FIG. 1 represents a graphic showing both endothelial and myocardiac gene expression in CD34+ cells, grown on the MV06 medium.

FIG. 1 represents the progressive expression by CD34+ cells of molecular biology markers either for endothelial (1A) or muscle cardiac cell (1B) progenitors when cultured on the MV06 medium.

Figure 2:
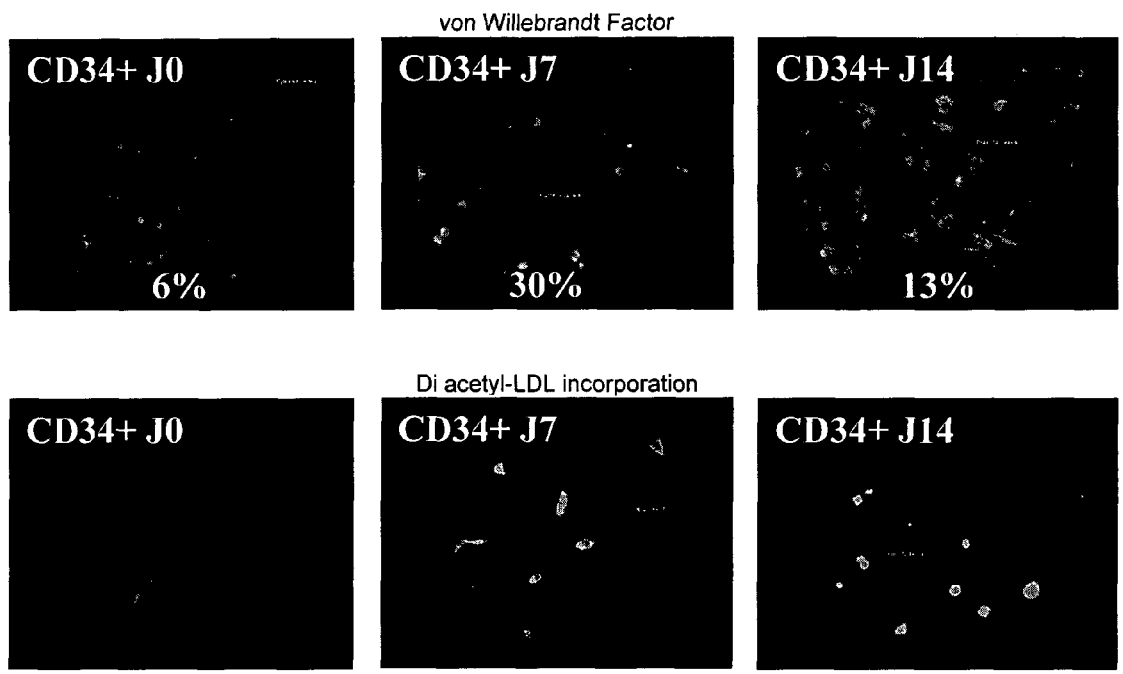
FIG. 2 represents photographs showing the results of growth, from CD34+ cells, of endothelial progenitor cells revealed by immunofluorescence.

FIG. 2 visualizes, by immunofluorescence, the progressive differentiation into endothelial cells of a part of CD34+ progenitor cells, grown in in vitro culture on the MV06 medium, labelled by anti-von Willebrandt Factor (vWF) antibody and diacetyl-LDL incorporation.

Figure 3:
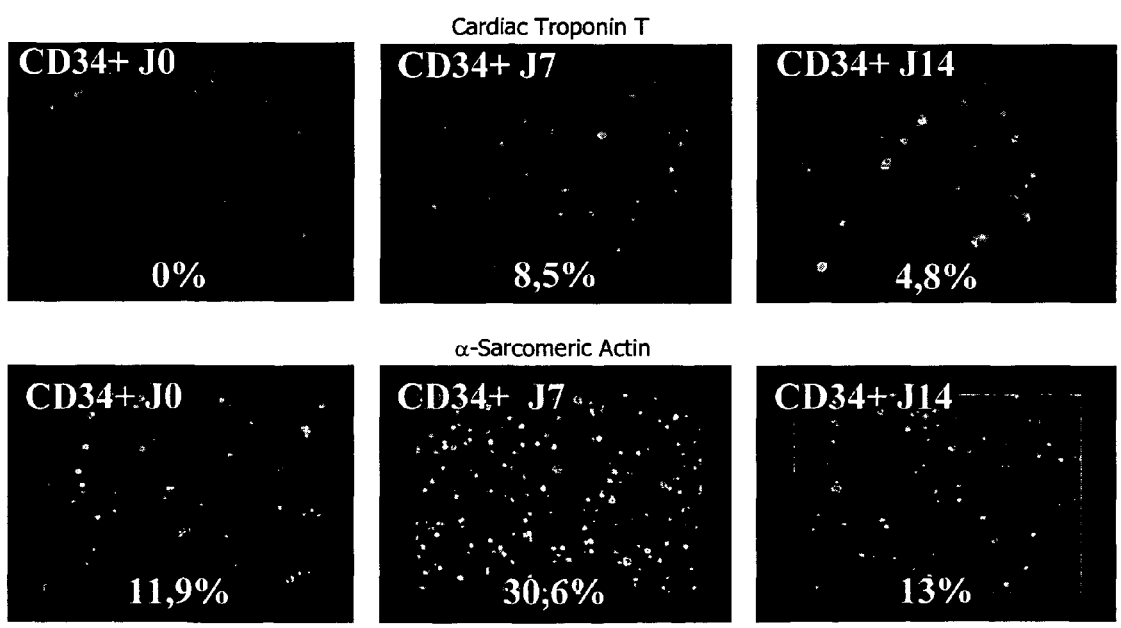
FIG. 3 represents photographs of immunofluorescence labelling of myocardiac cells growth from CD34+ cells.

FIG. 3 represent photographs of the results, obtained by immunofluorescence, of myocardiac cells grown from CD34+ cells on the culture medium of the invention, labelled by anti-Troponin T and by anti-α-Sarcomeric actin monoclonal antibodies.

According to the invention, the MV06 culture medium is composed of:

| | |
|---|---|
| Iscove's Modified Dubellco's Medium (GibcoBRL # 21980) | 83% |
| Fetal calf serum | 12.5% |
| Horse serum | 2.5% |
| L-Glutamin 200 mM (100X) | 1% |
| Penicillin (10000 u/mL)/Streptomycin (1000 μg/mL) | 1% |
| Hu-R Bone Morphogenetic Protein 2 (Eurobio) | 1 ng/mL |
| Hu-R Fibroblast Growth Factor 2 (Eurobio) | 5 ng/mL |
| Hu-R Vascular Endothelial Growth Factor (Eurobio) | 10 ng/mL |

And the culture is made on an extra-cell matrix composed of:

Fibronectin (solution from bovine plasma, SIGMA #F1141) 0.0005%

Gelatine (type B, from bovine skin, SIGMA #G1393) 0.02%

In a first phase, the MV06 culture medium, according to the invention, will only be used for evaluation of the CD34+ cells expansion. It is to be noted indeed that it comprises different components of animal origin (mainly bovine), making it unsuitable for a direct clinical use.

However, the possibility of substituting components of human origin in place of animal components is currently tested, so as to use further the culture medium according to the invention directly as cell expansion medium participating to the entire scheduled clinical procedure.

The invention claimed is:

1. A culture medium enabling growth in vitro of both endothelial progenitor and myocardiac progenitor cells from adult human stem cells comprising:
   Iscove's modified Dulbecco's medium;
   fetal calf serum;
   horse serum;
   200 mM L-Glutamine;
   Human recombinant Bone Morphogenetic Protein 2 (BMP-2);
   Human recombinant Fibroblast Growth Factor 2 (FGF2);
   Human recombinant Vascular Endothelial Growth Factor (VEGF); and
   10000 u/mL Penicillin and 1000 ug/mL Streptomycin.

2. The culture medium according to claim 1, wherein the Iscove's modified Dulbecco's medium represents 83% of a total volume of the culture medium.

3. The culture medium according to claim 1, wherein the fetal calf serum represents 12.5% of a total volume of the culture medium.

4. The culture medium according to claim 1, wherein the horse serum represents 2.5% of a total volume of the culture medium.

5. The culture medium according to claim 1, wherein the 200 mM L-Glutamine represents 1% of a total volume of the culture medium.

6. The culture medium according to claim 1, wherein the 10000 u/mL Penicillin and the 1000 ug/mL Streptomycin represent 1% of a total volume of the culture medium.

7. The culture medium according to claim 1, wherein the Human recombinant Bone Morphogenetic Protein 2 (BMP-2) has a concentration of 1 ng/mL.

8. The culture medium according to claim 1, wherein the basicHuman recombinant Fibroblast Growth Factor (FGF2) has a concentration of 5 ng/mL.

9. The culture medium according to claim 1, wherein the Human recombinant Vascular Endothelial Growth Factor (VEGF) has a concentration of 10 ng/mL.

10. A culture medium enabling growth in vitro of both endothelial progenitor and myocardiac progenitor cells from CD34+ cells, the culture medium consisting of:
    Iscove's modified Dulbecco's medium;
    fetal calf serum;
    horse serum;
    200 mM L-Glutamine;
    Human recombinant Bone Morphogenetic Protein 2 (BMP-2);
    Human recombinant Fibroblast Growth Factor 2 (FGF2);
    Human recombinant Vascular Endothelial Growth Factor (VEGF);
    10000 u/mL Penicillin and 1000 ug/mL Streptomycin; and
    the culture medium is laid on an extracellular matrix comprising:
        fibronectin; and
        gelatine.

11. The culture medium according to claim 10, wherein the fibronectin represents 0.0005% of a total volume of the extracellular matrix.

12. The culture medium according to claim 10, wherein the gelatine represents 0.02% of a total volume of the extracellular matrix.

13. The culture medium according to claim 12, wherein the gelatine is a type B gelatine derived from bovine skin.

14. The culture medium according to claim 1, wherein the Iscove's modified Dulbecco's medium represents 83% of a total volume of the culture medium;
- the fetal calf serum represents 12.5% of the total volume of the culture medium;
- the horse serum represents 2.5% of the total volume of the culture medium;
- the 200 mM L-Glutamine represents 1% of the total volume of the culture medium;
- the 10000 u/mL Penicillin and the 1000 ug/mL Streptomycin represent 1% of the total volume of the culture medium;
- the Human recombinant Bone Morphogenetic Protein 2 (BMP-2) has a concentration of 1 ng/mL;
- the basic Human recombinant Fibroblast Growth Factor (FGF2) has a concentration of 5 ng/mL; and
- the Human recombinant Vascular Endothelial Growth Factor (VEGF) has a concentration of 10 ng/mL.

15. The culture medium according to claim 14, wherein the culture medium is laid on an extracellular matrix comprising fibronectin and gelatine.

16. The culture medium according to claim 15, wherein the fibronectin represents 0.0005% of the total volume of the extracellular matrix.

17. The culture medium according to claim 15, wherein the gelatine represents 0.02% of the total volume of the extracellular matrix.

18. The culture medium according to claim 16, wherein the gelatine represents 0.02% of the total volume of the extracellular matrix.

19. The culture medium according to claim 15, wherein the gelatine is a type B gelatine derived from bovine skin.

20. A culture medium enabling growth in vitro of both endothelial progenitor and myocardiac progenitor cells from adult human stem cells, the culture medium consisting of:
- Iscove's modified Dulbecco's medium, which constitutes approximately 83% of a total volume of the culture medium;
- fetal calf serum, which constitutes approximately 12.5% of the total volume of the culture medium;
- horse serum, which constitutes approximately 2.5% of the total volume of the culture medium;
- 200 mM L-Glutamine, which constitutes approximately 1% of the total volume of the culture medium;
- Human recombinant Bone Morphogenetic Protein 2 (BMP-2) having a concentration of 1 ng/mL;
- Human recombinant Fibroblast Growth Factor 2 (FGF2) having a concentration of 5 ng/mL;
- Human recombinant Vascular Endothelial Growth Factor (VEGF) having a concentration of 10 ng/mL;
- 10000 u/mL Penicillin and 1000 ug/mL Streptomycin, which constitute approximately 1% of the total volume of the culture medium; and
- the culture medium being supported by an extracellular matrix comprising fibronectin and gelatine, the fibronectin constituting approximately 0.0005% of the total volume of the extracellular matrix and the gelatine is a type B gelatine derived from bovine skin and constitutes approximately 0.02% of the total volume of the extracellular matrix.

* * * * *